US008014538B2

(12) United States Patent
Onishi et al.

(10) Patent No.: US 8,014,538 B2
(45) Date of Patent: Sep. 6, 2011

(54) ACTIVE NOISE REDUCING DEVICE

(75) Inventors: Masahide Onishi, Osaka (JP); Yoshio Nakamura, Osaka (JP); Shigeki Yoshida, Mie (JP)

(73) Assignee: Panasonic Corporation, Osaka (JP)

( * ) Notice: Subject to any disclaimer, the term of this patent is extended or adjusted under 35 U.S.C. 154(b) by 691 days.

(21) Appl. No.: 11/573,380

(22) PCT Filed: Jul. 21, 2006

(86) PCT No.: PCT/JP2006/314450
§ 371 (c)(1),
(2), (4) Date: Feb. 7, 2007

(87) PCT Pub. No.: WO2007/011010
PCT Pub. Date: Jan. 25, 2007

(65) Prior Publication Data

US 2009/0279710 A1 Nov. 12, 2009

(30) Foreign Application Priority Data

Jul. 21, 2005 (JP) ................................ 2005-210921

(51) Int. Cl.
*G10K 11/16* (2006.01)
*H03B 29/00* (2006.01)
*A61F 11/06* (2006.01)

(52) U.S. Cl. ................................... 381/71.14; 381/71.4

(58) Field of Classification Search ............... 381/71.11, 381/71.4, 71.8, 71.1, 94.1, 94.9, 59, 57, 71.14
See application file for complete search history.

(56) References Cited

U.S. PATENT DOCUMENTS 7,574,006 B2 * 8/2009 Funayama et al. ......... 381/71.12
2004/0240678 A1 * 12/2004 Nakamura et al. ......... 381/71.11
2004/0247137 A1 12/2004 Inoue et al.

FOREIGN PATENT DOCUMENTS

| | | | |
|---|---|---|---|
| CN | 1573919 | A | 2/2005 |
| JP | 3-5255 | A | 1/1991 |
| JP | 4-342296 | A | 11/1992 |
| JP | 9-319381 | A | 12/1997 |
| JP | 10-174199 | A | 6/1998 |
| JP | 2000-99037 | A | 4/2000 |
| JP | 2004-354657 | A | 12/2004 |
| JP | 2004-361721 | A | 12/2004 |
| JP | 2005-10240 | A | 1/2005 |

OTHER PUBLICATIONS

Chinese Office Action for 2006800009705, Nov. 27, 2009.
Japanese language International Search Report for PCT/JP2006/314450, dated Oct. 3, 2006.

* cited by examiner

*Primary Examiner* — Curtis Kuntz
*Assistant Examiner* — Hai Phan
(74) *Attorney, Agent, or Firm* — RatnerPrestia

(57) ABSTRACT

An active noise reducing device includes switchover frequency memory which stores a speaker having weaker influence of level drop or dips in gain characteristics of transmission from first speaker and second speaker both working as secondary noise generators to microphone working as a residual signal detector, and also stores a frequency band of that speaker. Output switcher appropriately and selectively switches first speaker over to second speaker in response to the noise frequency at present calculated based on the rpm of engine by frequency calculator. This structure allows the active noise reducing device to work steadily even if level drop or a dip occurs in the gain characteristics of transmission from the speaker to the microphone, and allows suppressing the occurrence of abnormal sound due to divergence or distorted sound due to excessive output. Ideal noise reduction effect can be expected.

12 Claims, 6 Drawing Sheets

ACTIVE NOISE REDUCING DEVICE

This application is a U.S. National Phase Application of PCT International Application PCT/JP2006/314450.

TECHNICAL FIELD

The present invention relates to an active noise reducing device that introduces signals of opposite phase and equal in amplitude to unpleasant muffled sound generated in a vehicle interior by a vehicle engine so that the introduced signals can interfere with the muffled sound, thereby reducing the unpleasant muffled sound.

BACKGROUND ART

A conventional active noise reducing device, well suited particularly for vehicles, employs an adaptation feed-forward control method using an adaptive notch filter for reducing unpleasant muffled engine sound generated in a vehicle interior accompanying the driving of an engine. This conventional device includes a residual signal detector having a microphone rigidly mounted in the interior, a secondary noise generator having a speaker rigidly mounted also in the interior. The secondary noise generator placed permanently at the same location as the residual signal detector is combined with the detector in order to reduce the subject noise collected at the location of the detector. This prior art is disclosed in, e.g. Unexamined Japanese Patent Publication No. 2000-99037.

However, in the environment of a limited space of the interior, deep dips or sharp peaks sometimes occur in the gain characteristics of transmission from the secondary noise generator including the speaker to the residual signal detector including the microphone. These dips and peaks are caused by interference or reflection of sound-wave in the small interior space, and they are generated regardless of the locations of the residual signal detector and the secondary noise generator. The active noise reducing device in accordance with the prior art employs the secondary noise generator placed permanently at the same place as the residual signal detector for reducing the subject noise detected at the place of the residual signal detector. Thus there is great possibility that dips and peaks occur in the gain characteristics of the transmission from the secondary noise generator to the residual signal detector within the frequency band to which the noise reduction control is desirably applied. Within the frequency band where the dips and peaks occur, the transmission phase characteristics also changes sharply and the occurrence frequency per se has a great dispersion. The noise reduction control to be carried out in such a frequency band tends to invite unstable operation of the adaptive filter, so that ideal noise-reduction effect cannot be expected. In the worst case, the adaptive filter falls in divergent state and generates abnormal sound. On top of that, in such a frequency band, the secondary noise generated by the secondary noise generator is hard to reach to the residual signal detector, so that an output from the active noise reducing device increases and the secondary noise generator produces distorted sound.

DISCLOSURE OF INVENTION

The present invention addresses the foregoing problems, and aims to provide an active noise reducing device that can operate steadily and produce ideal noise reduction effect at the frequency which needs the noise reduction, and in the case where dips/peaks occur in the gain characterstics of the transmission from secondary noise generators including speakers to a residual signal detector including a microphone. The active noise reducing device of the present invention also can suppress the occurrence of abnormal sound due to divergence or distorted sound due to excessive output in the foregoing state.

The active noise reducing device of the present invention comprises the following elements:

- a cosine wave generator for generating a cosine wave signal synchronized with a frequency of actual;
- a sine wave generator for generating a sine wave signal synchronized with the frequency of the noise;
- a first one-tap adaptive filter for receiving a reference cosine wave signal output from the cosine wave generator;
- a second one-tap adaptive filter for receiving a reference sine wave signal output from the sine wave generator;
- an adder for adding the output signal from the first one-tap adaptive filter to the output signal from the second one-tap adaptive filter;
- a plurality of secondary noise generators for generating secondary noises by using output signals from the adder;
- a switcher placed between the adder and the plurality of secondary noise generators for selectively switching one of the plurality of secondary noise generators over to another one;
- a residual signal detector for detecting a residual signal produced by interference between the secondary noises and the noise, which secondary noises are generated by the secondary noise generator selected by the switcher;
- a simulated signal generator, including a plurality of correction values simulating the transmission characteristics from the plurality of the secondary noise generators to the residual signal detector, for outputting a simulated cosine wave signal and a simulated sine wave signal, both corrected with the correction value between the secondary noise generator, which receives the reference cosine wave signal and the reference sine wave signal and is selected by the switcher, and the residual signal detector; and
- a coefficient updating section for updating respective filter coefficients of the first one-tap adaptive filter and the second one-tap adaptive filter so that the noises at the residual signal detector can be minimized by the respective output signals from the residual signal detector and the simulated signal generator.

The foregoing structure allows the active noise reducing device to work steadily at the frequency which needs the noise reduction and in the case where dips/peaks occur in the gain characteristics of the transmission from the secondary noise generators including speakers to the residual signal detector including the microphone. In the foregoing state, the active noise reducing device also suppresses the occurrence of abnormal sound due to divergence and distorted sound due to excessive output, so that ideal noise reduction effect can be obtained.

DESCRIPTION OF REFERENCE MARKS

Figure 1:
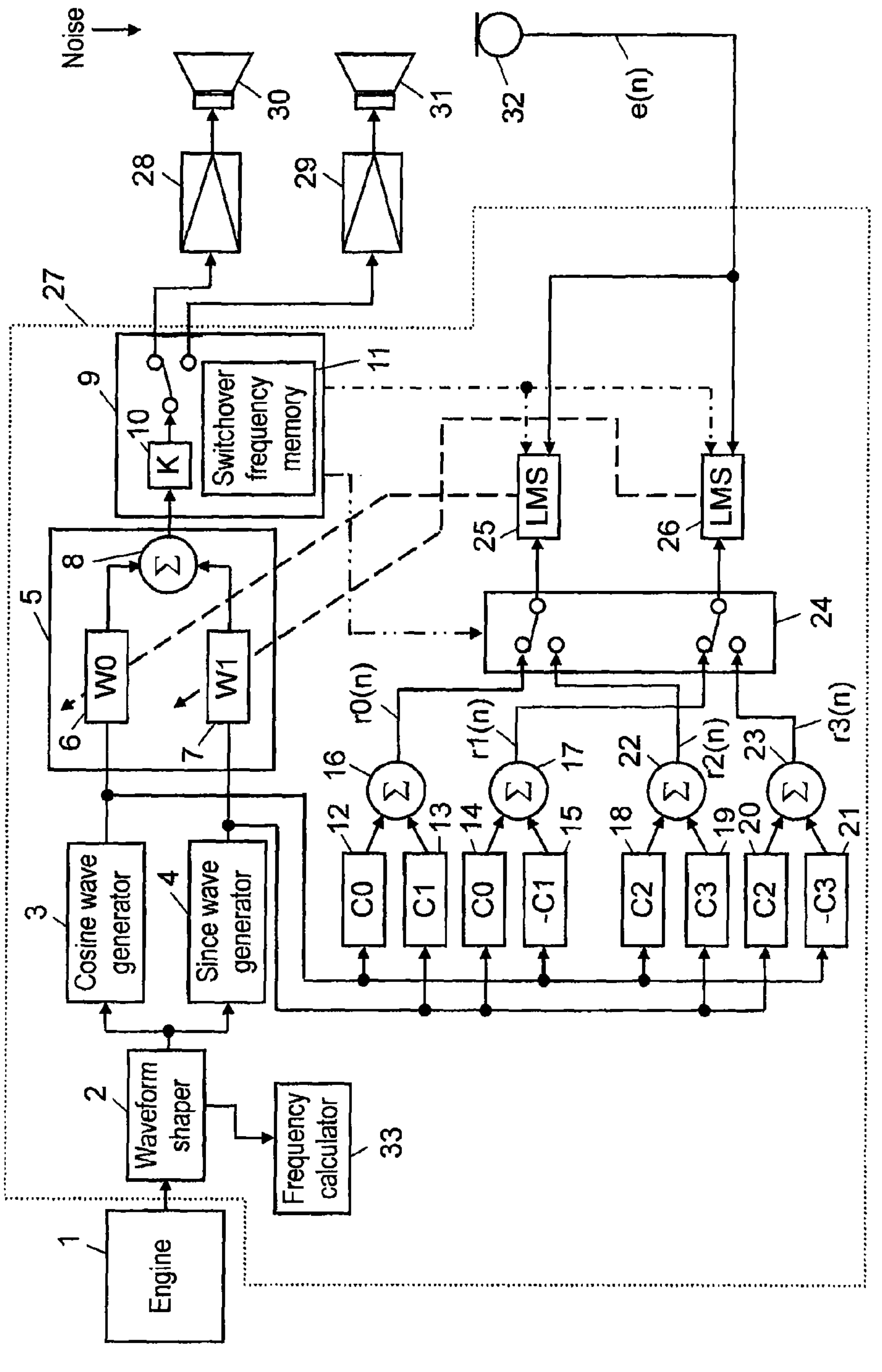
FIG. 1 shows a block diagram illustrating a structure of an active noise reducing device in accordance with a first embodiment of the present invention.

1 engine
3 cosine wave generator
4 sine wave generator
5 adaptive notch filter
6 first one-tap adaptive filter
7 second one-tap adaptive filter
8, 16, 17, 22, 23 adder
9 output switcher (switcher)
10 multiplier
12, 13, 14, 15 transmission element as a first corrected value (simulated signal generator)
18, 19, 20, 21 transmission element as a second corrected value (simulated signal generator)
24 simulated signal selector
25, 26 adaptive control algorithm calculator (coefficient updater)
27 discrete signal processor
28 first power amplifier (secondary noise generator)
29 second power amplifier (secondary noise generator)
30 first speaker (secondary noise generator)
31 second speaker (secondary noise generator)
32 microphone (residual signal detector)

DESCRIPTION OF PREFERRED EMBODIMENTS

Exemplary embodiments of the present invention are demonstrated hereinafter with reference to the accompanying drawings. The demonstration is done in this way: the active noise reducing device of the present invention is mounted to a vehicle such as a car, and vibration of the engine causes to produce unpleasant noises in the interior, then the device reduces the noises.

Embodiment 1

FIG. 1 shows a block diagram illustrating a structure of an active noise reducing device in accordance with the first embodiment of the present invention. In FIG. 1, engine 1 forms a noise source, and discrete signal processor 27 such as a digital signal processor or a microprocessor generates signals, which cancel out the noise, by using software, thereby carrying out the noise reducing control.

This active noise reducing device works such that the device reduces the noise having conspicuous periodicity synchronized with the rpm of engine 1. The subject noise is similar to the noise generated by propagation of the exciting force produced by driving engine 1 through the car body. For instance, an engine of 4-cycle and 4-cylinder produces noise, called secondary component of the rotation, which noise has a frequency two times of the rpm of the engine and is the target of the control. This target noise is generated by a change in torque, and this change is produced by combustion of gas generated every ½ rotation of the engine crank. In other words, the exciting vibration generated from the engine produces the noise in the interior, and this noise has strong muffled impression, so that the noise makes people in the interior feel unpleasant.

An engine pulse synchronized with the rotation of engine 1 is supplied to waveform shaper 2, where noise superposed on the pulse is removed and the pulse wave is shaped. The engine pulse employs an output signal from a top-dead-end sensor or a tacho-pulse. In the case of using the tacho-pulse as the engine pulse, since the tacho-pulse is often available as an input signal to a tachometer equipped in the vehicle, it does not require a dedicated device to this purpose, so that use of the tacho-pulse will suppress the increase of the cost.

An output signal from waveform shaper 2 is supplied to frequency calculator 33, cosine wave generator 3, and sine wave generator 4. Frequency calculator 33 calculates, by using the rpm information of engine 1, a notch frequency to be damped (hereinafter referred to simply as "notch frequency"). Generators 3 and 4 generate a cosine wave and a sine wave as reference signals synchronized with the obtained notch frequency.

Cosine wave generator 3 outputs the reference cosine wave signal, which is multiplied by filter coefficient W0 of first one-tap adaptive filter 6 in adaptive notch filter 5. Since wave generator 4 outputs the reference sine wave signal, which is multiplied by filter coefficient W1 of second one-tap adaptive filter 7 in adaptive notch filter 5. Both of the output signals from filters 6 and 7 are added together by adder 8.

First power amplifier 28 and first speaker 30, second power amplifier 29 and second speaker 31 work as secondary noise generators which radiate the output signal from adder 8, i.e. the output signal from adaptive notch filter 5, as the secondary noise in the interior for canceling out the noise. First speaker 30 and second speaker 31 are placed in the interior at stationary spots. To be more specific in this case, first speaker 30 employs a front-door speaker equipped in advance to the vehicle for reproducing audio signals. Second speaker 31 employs a rear-tray speaker equipped also in advance to the vehicle for reproducing audio signals.

A conventional general-use active noise reducing device uses a speaker stationary positioned for generating secondary noises. This is already explained in the background art. Thus the active noise reducing control always employs either one of first speaker 30 or second speaker 31. The demonstration hereinafter uses first speaker 30 at all times for generating the secondary noise.

The secondary noise radiated from first speaker 30 interferes with the subject noise, thereby deadening the subject noise; however, the interference does not completely deaden the subject noise, and some residual signals still remain. The residual signals are detected by microphone 32 working as the residual signal detector, and they can be used as error signals "e" (n) in adaptive control algorithm for updating filter coefficients W0 and W1 of adaptive notch filter 5, where (n) is a natural number and indicates the number of repetition of the algorithm.

A simulated signal generator comprises transmission elements 12, 13, 14 and 15 working as first correction values, and adders 16, 17. This generator simulates the transmission characteristics from first power amplifier 28 to microphone 32 at the notch frequency. First, the reference cosine wave signal is supplied to transmission element 12, and the reference sine wave signal is supplied to transmission element 13. Then the outputs from elements 12 and 13 are added together by adder 16, thereby generating first simulated cosine wave signal "r0" (n), which is supplied to adaptive control algorithm calculator 25 and used in the adaptive control algorithm for updating filter coefficient W0 of first one-tap adaptive filter 6.

In a similar way, the reference sine wave signal is supplied to transmission element 14, and the reference cosine wave signal is supplied to transmission element 15. Then the outputs from elements 14 and 15 are added together by adder 17, thereby generating first simulated sine wave signal "r1" (n), which is supplied to adaptive control algorithm calculator 26 and used in the adaptive control algorithm for updating filter coefficient W1 of second one-tap adaptive filter 7.

Filter coefficients W0 and W1 of adaptive notch filter 5 are updated, in general, based on the least mean square (LMS) algorithm, a kind of steepest descent methods. At this time, filter coefficients W0 (n+1) and W1 (n+1) can be found by the following equations:

$$W0(n+1)=W0(n)-\mu\times e(n)\times r0(n) \quad (1)$$

$$W1(n+1)=W1(n)-\mu\times e(n)\times r1(n) \quad (2)$$

where "μ" is a step size parameter.

Coefficients W0 (n+1) and W1 (n+1) thus recursively converge into an optimum value such that error signal "e"(n) becomes smaller, i.e. the noise at microphone 32 decreases.

As discussed above, use of the speaker stationary positioned for the noise reducing control is effective when no level drop, no deep dips, or no sharp peaks are found in the gain characteristic of the transmission from the speaker (secondary noise generator) to the microphone (residual signal detector) at the frequency band to be controlled. However, in the environment of the vehicle interior where the active noise reducing device is actually used, numerous dips and peaks peculiar to the small interior exist in the transmission gain characteristics. These dips and peaks occur due to reflection and interference of sound waves generated in the interior.

Figure 2:
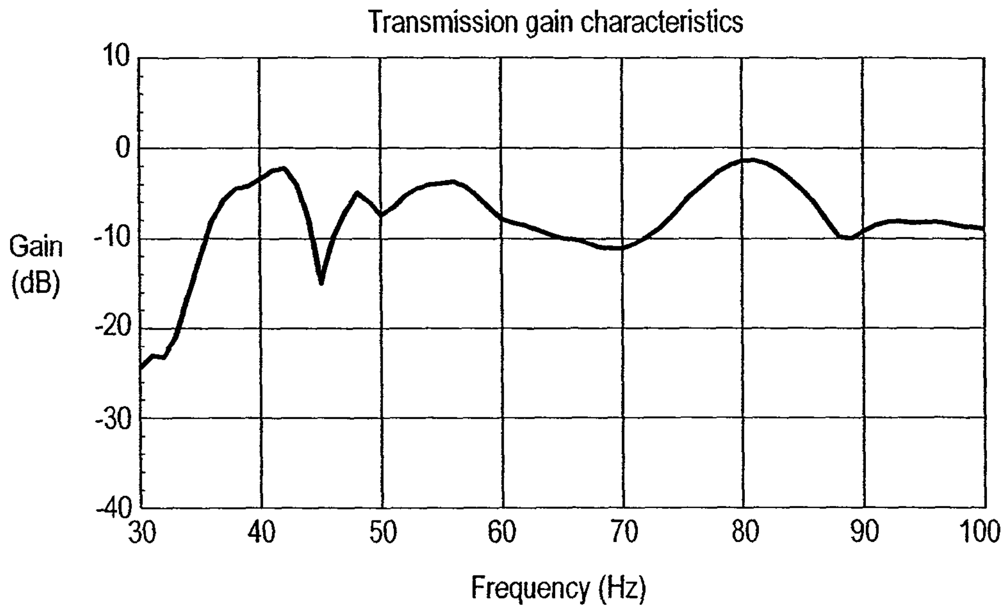
FIG. 2 shows a gain characteristic of the transmission from a first speaker to a microphone of the active noise reducing device in accordance with the first embodiment of the present invention.

FIG. 2 shows a gain characteristic of transmission from the first speaker to the microphone of the active noise reducing device in accordance with the first embodiment of the present invention. This is an example of the transmission gain characteristics in the vehicle interior, i.e. the gain characteristics of transmission from first speaker 30 placed at a front door as the secondary noise generator to microphone 32 placed at a map lamp near the front seat as the residual signal detector. FIG. 2 tells that below 35 Hz shows a gain drop accompanying the output fall of first speaker 30 per se, and over 35 Hz particularly at the band between 43 Hz and 47 Hz, a large dip occurs.

Figure 3:
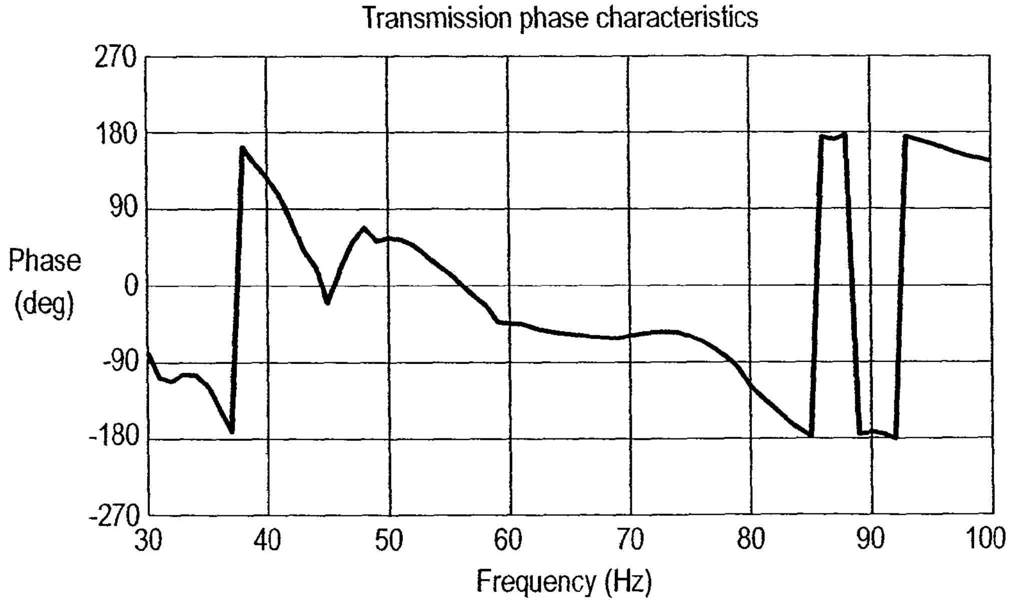
FIG. 3 shows a phase characteristics of the transmission from the first speaker to the microphone of the active noise reducing device in accordance with the first embodiment of the present invention.

FIG. 3 shows a phase characteristics of the transmission from the first speaker to the microphone of the active noise reducing device in accordance with the first embodiment of the present invention. FIG. 3 tells that a drastic change in the transmission phase characteristics occurs particularly at the band between 43 Hz and 47 Hz. The dip at this band occurs due to reflection and interference of sound waves generated in the interior. Subtle changes in the environment, where the active noise reducing device is actually used, greatly affect and vary the occurrence frequency. The subtle changes include aged deterioration in the characteristics of first speaker 30 or microphone 32, a change in the number of people in the vehicle, open/close of the windows. The variation in the occurrence frequency is accompanied by a great change in the transmission phase characteristics, thereby producing a greater deviation from the correction value of the simulated signal generator. As a result, adaptive notch filter 5 works unsteadily. In the worst case, people in the interior can hear abnormal sound due to divergence. On top of that, at a such frequency band, the secondary noise radiated from first speaker 30 is hard to reach to microphone 32, so that an output from the active noise reducing device becomes inevitably greater, and first speaker 30 thus generates distorted sound.

There is a need for ensuring steady operation of the adaptive notch filter and for suppressing abnormal operation such as divergence even if a level drop, dips or peaks are found in the gain characteristics of the transmission from the speaker working as the secondary noise generator to the microphone working as the residual signal detector.

The active noise reducing device in accordance with the first embodiment includes a plurality of the secondary noise generators which radiate output signals from adaptive notch filter 5 as the secondary noises, and a switcher that selectively switches one of the plurality of the secondary noise generators over to another one. An appropriate switchover of the secondary noise generators allows suppressing the divergence of adaptive notch filter 5, and obtaining stable effect of noise reduction.

To obtain the foregoing effects, the active noise reducing device includes adder 8, and output switcher 9 placed between first power amplifier 28 and second power amplifier 29 both working as the secondary noise generator. Output switcher 9 selectively switches first speaker 30 over to/from second speaker 31 whichever radiates the output signal supplied from adaptive notch filter 5. Switcher 9 includes therein coefficient K of multiplier 10 and switchover frequency memory 11 storing the frequency (hereinafter referred to as a switchover frequency) at which first speaker 30 is switched to/from second speaker 31. Coefficient K of multiplier 10 is used as a multiplier to an output signal from adder 8, i.e. an input signal to switcher 9, and takes a value of "1" when switcher 9 is out of the switching operation described later. Switcher 9 always compares the present notch frequency calculated by frequency calculator 33 with the switchover frequency stored in memory 11, and selects one of first speaker 30 or second speaker 31 appropriately.

Figure 4:
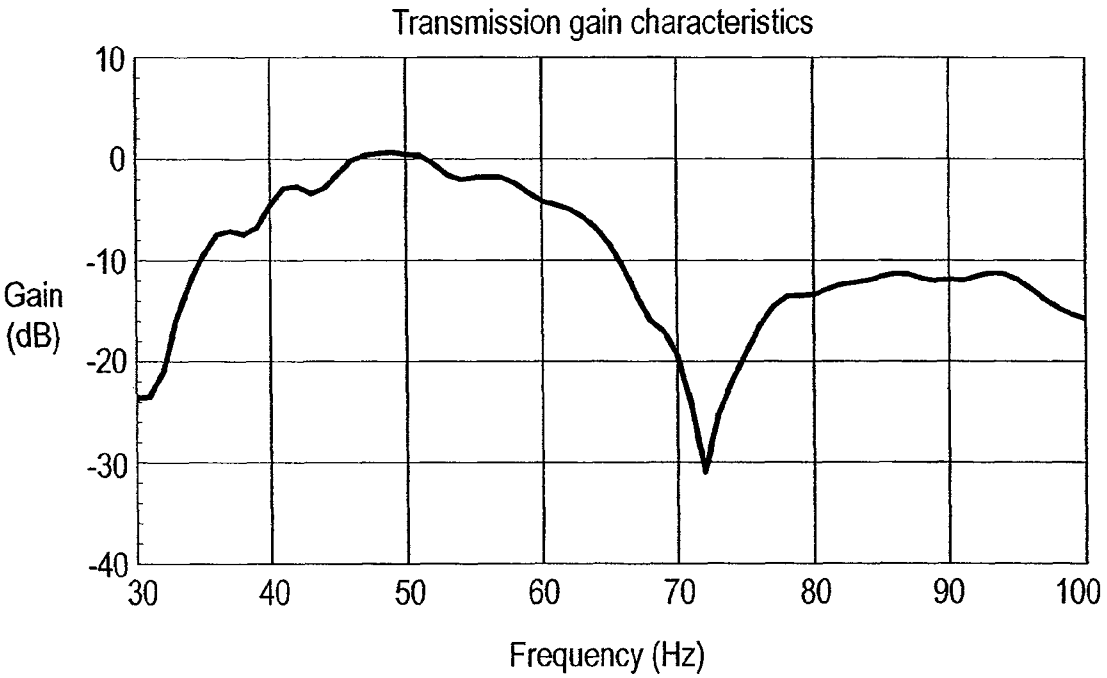
FIG. 4 shows a gain characteristic of the transmission from a second speaker to the microphone of the active noise reducing device in accordance with the first embodiment of the present invention.

FIG. 4 shows a gain characteristic of transmission from the second speaker to the microphone of the active noise reducing device in accordance with the first embodiment of the present invention. This is another example of the transmission gain characteristics in the vehicle interior, namely, the gain characteristics of the transmission from second speaker 31 working as the secondary noise generator and placed at the rear tray to microphone 32 working as the error signal detector placed near the map lamp at the front seat. This the same as previously discussed. Comparison of FIG. 2 with FIG. 4 tells that no dips are found in FIG. 4 at the band between 43 Hz and 47 Hz although they are found in FIG. 2, and in the band up to 65 Hz second speaker 31 placed at the rear tray transmits greater sound to microphone 32 than first speaker 30 placed at the front door. Second speaker 31 is thus more useful for the noise reducing control than first speaker 30.

In the case of working this active noise reducing device within the frequency range from, e.g. 40 Hz to 80 Hz, first speaker 30 is used at the band ranging from not less than 40

Hz to less than 43 Hz, and second speaker 31 is used in the frequency band raging from not less than 43 Hz to less than 60 Hz, again first speaker 30 is used in the frequency band ranging from not less than 60 Hz to not higher than 80 Hz. This work-sharing of the speakers allows eliminating adverse influence of level drops or dips in the transmission gain characteristics all over the frequency band undergoing the noise reducing control. Switchover frequency memory 11 placed in output switcher 9 thus should store 43 Hz and 60 Hz as switchover frequencies, and it should also store which speaker is used at which frequency band.

For instance, in a stationary case where frequency calculator 33 calculates that a frequency of the present noise is 41 Hz, output switcher 9 selects first speaker 30 based on the information supplied from frequency memory 11. At this time, coefficient "K" of multiplier 10 takes a value of "1". In the pre-stage to adaptive control algorithm calculators 25 and 26, simulated signal selector 24 is placed, which selects first simulated cosine wave signal "r0" (n) and first simulated sine wave signal "r1" (n) from first speaker 30 presently selected to microphone 32. Selector 24 is a switch for selecting, by using a switching signal supplied from switcher 9, the simulated cosine wave signal or the simulated sine wave signal which simulate the transmission characteristics from the speaker, which is switched over by switcher 9 and works as the secondary noise generator, to microphone 32.

Then assume that engine 1 increases its rpm, and the subject frequency changes to 50 Hz. Switchover frequency memory 11 compares the stored switchover frequencies with the present frequency (50 Hz) and determines to switch the speaker to second speaker 31, then starts the switching. However, a sudden switchover by output switcher 9 incurs abnormal sound like "bottu" from first speaker 30 that has been working as the secondary noise generator, or allows adaptive notch filter 5 to fall into unsteady control because filter 5 cannot follow the sudden change in the sound field.

To overcome the foregoing problem, when switchover frequency memory 11 determines the switchover of the speaker, memory 11 outputs a signal to adaptive algorithm calculators 25 and 26 for halting an adaptive calculation temporarily. Then the coefficient of multiplier 10 is approximated from the present value "1" to "0" step by step, so that the secondary noise radiated from first speaker 30 fades. After the coefficient reaches to "0", switcher 9 switches the speaker over to second speaker 31, and at the same time, the switch of simulated signal selector 24 outputs a switchover signal for switching the speaker over to second speaker 31. Then the coefficient of multiplier 10 is reset to "1" again, and the calculation of adaptive algorithm calculators 25, 26 is restarted.

A signal simulating the transmission characteristics from second speaker 31, which is selected by simulated signal selector 24 and used by adaptive algorithm calculators 25 and 26, to microphone 32 is described hereinafter.

The simulated signal generator comprises transmission elements 18, 19, 20, 21 working as second correction values, and adders 22, 23. Similar to the case using first speaker 30, this generator 24 simulates the transmission characteristics from second power amplifier 29 to microphone 32 at the notch frequency. First, the reference cosine wave signal is supplied to transmission element 18, and the reference sine wave signal is supplied to transmission element 19. Then the outputs from elements 18 and 19 are added together by adder 22, thereby generating second simulated cosine wave signal "r2" (n), which is supplied to adaptive control algorithm calculator 25 and used in the adaptive control algorithm for updating filter coefficient W0 of first one-tap adaptive filter 6.

In a similar way, the reference sine wave signal is supplied to transmission element 20, and the reference cosine wave signal is supplied to transmission element 21. Then the outputs from elements 20 and 21 are added together by adder 23, thereby generating second simulated sine wave signal "r3" (n), which is supplied to adaptive control algorithm calculator 26 and used in the adaptive control algorithm for updating filter coefficient W1 of second one-tap adaptive filter 7.

Filter coefficients W0 (n+1) and W1 (n+1) of adaptive notch filter 5 can be found similarly to equations (1) and (2), i.e. by the following equations:

$$W0(n+1)=W0(n)-\mu\times e(n)\times r2(n) \tag{3}$$

$$W1(n+1)=W1(n)-\mu\times e(n)\times r3(n) \tag{4}$$

where "μ" is a step size parameter.

Assume that the rpm of engine 1 increases to 70 Hz, then switchover frequency memory 11 starts switching second speaker 31 presently used over to first speaker 30 again. The switchover procedure is similar to what is discussed above.

Embodiment 2

Figure 5:
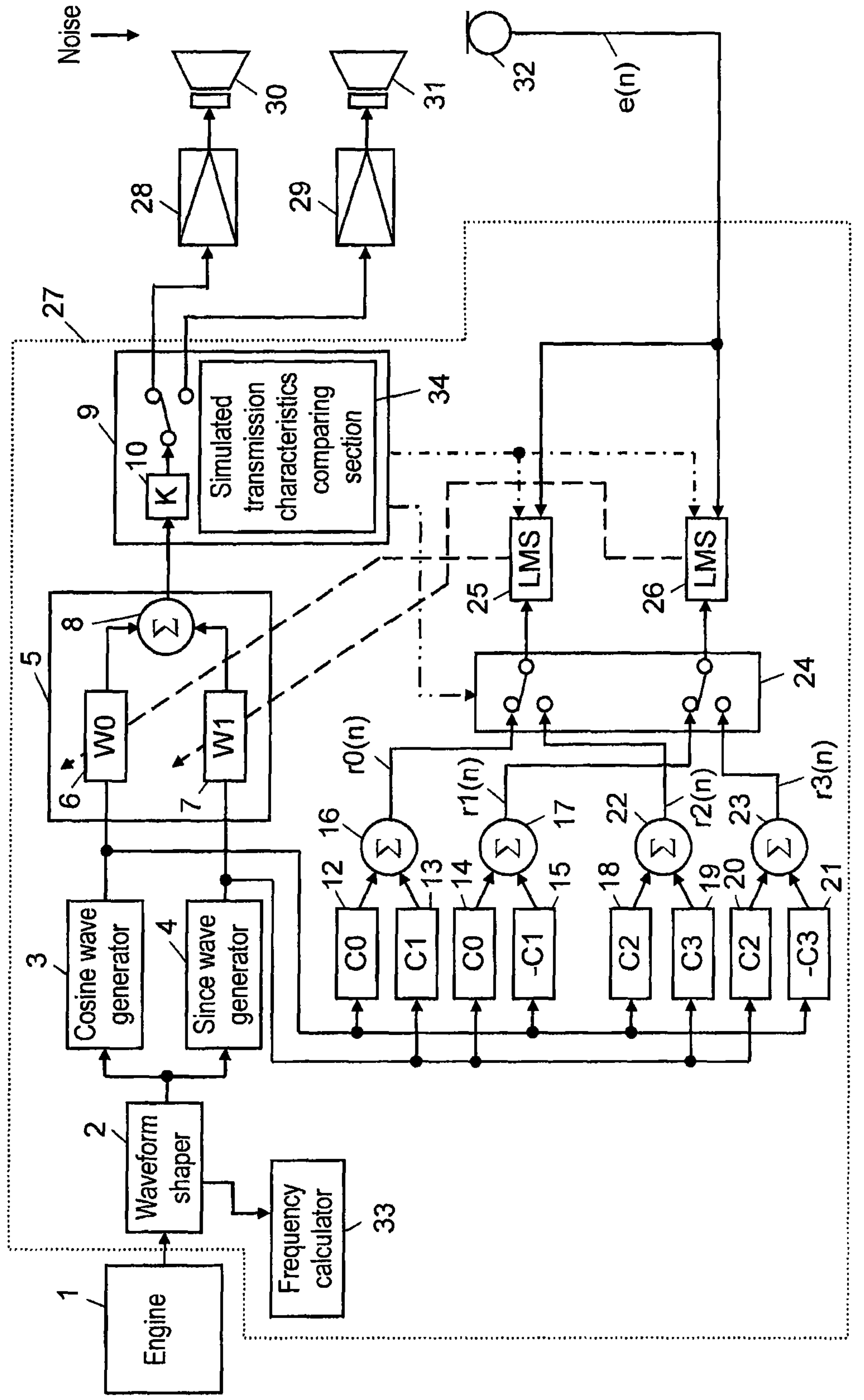
FIG. 5 shows a block diagram illustrating a structure of an active noise reducing device in accordance with a second or a third embodiment of the present invention.

FIG. 5 shows a block diagram illustrating a structure of an active noise reducing device in accordance with the second embodiment of the present invention. Similar elements to those used in the first embodiment have the same reference marks, and the descriptions thereof are omitted here.

The first embodiment discussed previously employs the following method: The gain characteristics of transmission from first speaker 30 to microphone 32, and the gain characteristic of transmission from second speaker 31 to microphone 32 are measured in advance with measuring instruments, and based on the measurement, switchover frequency memory 11 placed in output switcher 9 stores in advance the switchover frequencies and the speakers to be used. In this second embodiment, the active noise reducing device per se determines the matters concerning the switchover.

FIG. 5 differs from FIG. 1 only in simulated transmission comparing section 34 which replaces switchover frequency memory 11. This change derives from this: while memory 11 stores in advance the frequencies to be switched and the speakers to be used at the switchover, in the second embodiment the active noise reducing device can determine by itself the speakers to be used one by one at a switchover. Operation of this simulated transmission comparing section 34 is specifically demonstrated hereinafter.

Frequency calculator 33 calculates a frequency of the subject noise, and every time the noise frequency changes, simulated transmission comparing section 34 calculates gain characteristics of the respective transmission characteristics, i.e. transmission characteristics from first speaker 30 to microphone 32 at the present frequency, an the one from second speaker 31 to microphone 32 at the present frequency. In those calculations comparing section 34 uses C0, C1 which are first correction values of transmission elements 12, 13, and these values simulate the transmission characteristics from first speaker 30 to microphone 32 at the present frequency. In the foregoing calculations, comparing section 34 also uses C2, C3 which are second correction values of transmission elements 18, 19, and these values simulate the transmission characteristics from second speaker 31 to microphone 32 at the present frequency. Gain characteristics of the transmission from first speaker 30 to microphone 32 are referred to as G1, and that from second speaker 31 to microphone 32 is referred to as G2. Then G1 and G2 can be found by the following equations:

$$G1=20\times\log_{10}(\sqrt{(C0^2+C1^2)})[\text{dB}] \quad (5)$$

$$G2=20\times\log_{10}(\sqrt{(C2^2+C3^2)})[\text{dB}] \quad (6)$$

Based on the values of G1 and G2, comparing section 34 selects the speaker to be used presently. To be more specific, the speaker that makes G1 or G2 maximum at the present frequency is selected. Because the speaker having a greater gain characteristics of the transmission from the speaker to the microphone can produce greater noise reduction effect in the active noise reducing control.

In the block diagram shown in FIG. 5, since there are only two speakers, i.e. first speaker 30 and second speaker 31, the speaker making G1 or G2 maximum is equal to the speaker having the greater gain characteristics. However, in the case of three or more than three speakers ("n" speakers) being available, the speaker that makes one of "n" gain characteristics, namely, G1, G2, G3, . . . , Gn, maximum is selected. The "n" gain characteristics can be found in a similar way to equations (5) and (6).

Figure 6:
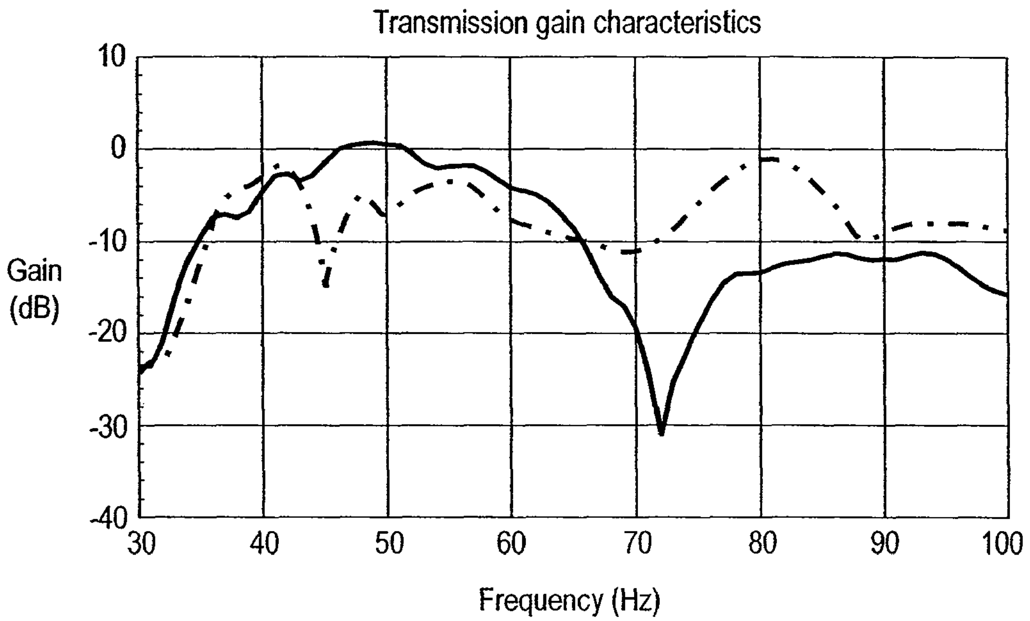
FIG. 6 shows both of the transmission gain characteristics shown in FIG. 2 and FIG. 4 simultaneously.

FIG. 6 shows both of the transmission gain characteristics shown in FIG. 2 and FIG. 4 simultaneously. In FIG. 6, the gain characteristics shown in FIG. 2 of the transmission from first speaker 30 to microphone 32 is drawn with an alternate long and short dash line, and the gain characteristics shown in FIG. 4 of the transmission from second speaker 31 to microphone 32 is drawn with a solid line.

Similar to the first embodiment, assume that the active noise reducing device shown in FIG. 5 works in the frequency range from 40 Hz to 80 Hz.

Assume that frequency calculator 33 calculates that the frequency of present noise is 45 Hz, and this is a stationary status. Simulated characteristics comparing section 34 receives this calculation result, and then calculates G1, G2 by using the first correction values C0, C1 of transmission elements 12, 13 at 45 Hz, which is the subject frequency to be controlled, as well as by using the second correction values C2, C3 of transmission elements 18, 19 at 45 Hz. In this case, the calculation finds that G1=−15 [dB], and G2=−2 [dB]. The respective values agree with the values at 45 Hz in FIG. 6. Because C0, C1, C2, and C3 are found from the following equations based on the gain characteristics and the phase characteristics of the transmission from the speaker to the microphone. Both of the characteristics have been measured with measuring instruments in advance. To be more specific, the gain and the phase of the transmission from first speaker 30 to microphone 32, both of the gain and the phase are measured with the measuring instrument, are referred to as "Gain 1" and "Phase 1", and in a similar way, the gain and the phase of the transmission from second speaker 31 to microphone 32, both of which gain and phase are measured with the measuring instrument, are referred to as "Gain 2" and "Phase 2". Then the following equations are obtainable:

$$C0=\text{Gain }1\times\cos(\text{Phase }1) \quad (7)$$

$$C2=\text{Gain }1\times\sin(\text{Phase }1) \quad (8)$$

$$C2=\text{Gain }2\times\cos(\text{Phase }2) \quad (9)$$

$$C3=\text{Gain }2\times\cos(\text{Phase }2) \quad (10)$$

At the present frequency 45 Hz to be controlled, simulated transmission comparing section 34 compares G1 with G2, and finds that G2 is greater (maximum), so that comparing section 34 determines second speaker 31 should be selected. Then the optimum speaker at this moment, namely, second speaker 31 is used for the active noise reducing control.

Every time the frequency of the subject noise changes, which frequency is calculated by frequency calculator 33, comparing section 34 do a similar calculation for selecting the speaker which produces the greatest transmission gain at the moment. After the selection of the presently optimum speaker, comparing section 34 will switch over the speaker in a similar way to what is discussed in the first embodiment.

First, a signal is sent to adaptive algorithm calculators 25 and 26 for halting temporarily an adaptive calculation. Then the coefficient of multiplier 10 is approximated from the present value "1" to "0" step by step, so that the secondary noise radiated from the speaker presently selected fades. After the coefficient reaches to "0", switcher 9 switches the speaker over to second speaker 31, and at the same time, the switch of simulated signal selector 24 outputs a switchover signal for switching the speaker over to another speaker newly selected. Then the coefficient of multiplier 10 is reset to "1" again, and the calculation of adaptive algorithm calculators 25, 26 is restarted. The foregoing operation allows preventing abnormal sound like "bottu" from occurring at an abrupt switchover of the speaker.

Figure 7:
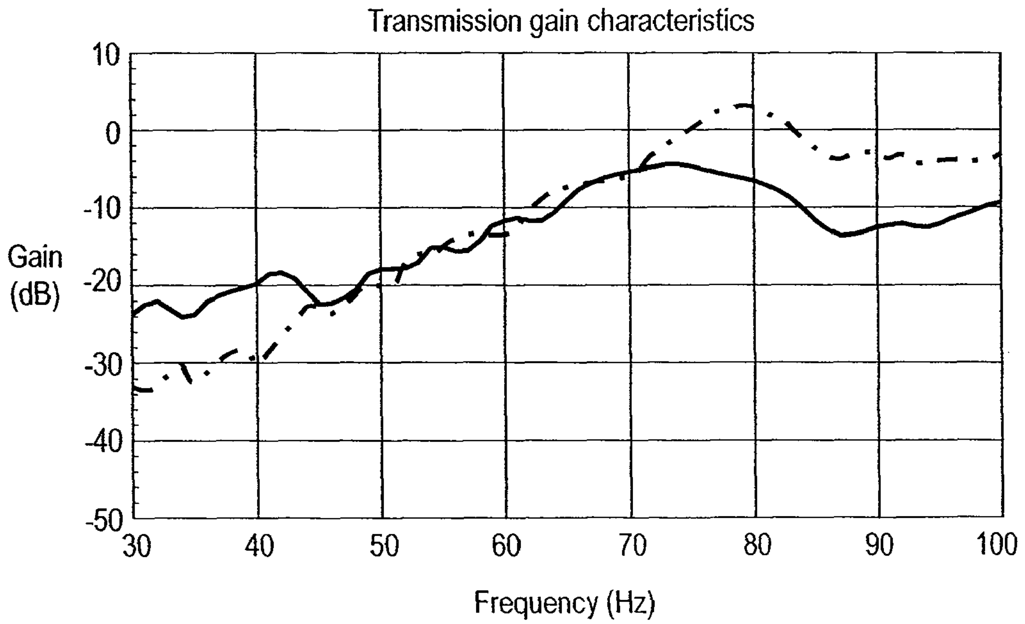
FIG. 7 shows both of the two transmission gain characteristics simultaneously, namely, gain characteristics of the transmission from the first speaker to the microphone of the active noise reducing device shown in FIG. 5 in accordance with the second embodiment, and that from the second speaker to the microphone.

FIG. 7 shows both of the two transmission gain characteristics simultaneously, namely, gain characteristics of transmission from the first speaker to the microphone of the active noise reducing device shown in FIG. 5 in accordance with the second embodiment, and that from the second speaker to the microphone. As shown in FIG. 6, within an operating frequency range of the active noise reducing device, when there is a distinct difference between the respective gain characteristics of transmission from the selectable speakers to the microphone, changes in the noise frequency do not cause frequent switchovers of the speakers, but the speaker keeps being selected.

However, as shown in FIG. 7, when the respective gain characteristics exist in frequency ranges similar to each other, selection of the speaker producing the maximum gain invites frequent switchovers of the speakers, so that sufficient noise reduction effect cannot be expected. In such a case, the frequent switchovers should be prevented.

Thus every time the noise frequency calculated by frequency calculator 33 changes, simulated transmission comparing section 34 compares gain characteristics "G now" with maximum gain characteristics "G max", and comparing section 34 starts switching the speaker over to another speaker only when "G max" is greater than "G now" by a given threshold value. "G now" is defined as the gain characteristics of the transmission from the speaker presently selected at the present frequency to the microphone, and "G max" is defined as the maximum gain characteristics of transmission from all the speakers selectable at the present frequency to the microphone.

The gain characteristics shown in FIG. 7 is taken as an example for the following specific demonstration, and it is assumed in this example that the active noise reducing device shown in FIG. 5 works within the frequency range from 40 Hz to 80 Hz, and also assumed that the threshold value (the given value) of the difference between the respective gain characteristics for switching over the speaker is 6 [dB]. In FIG. 7, the alternate long and short dash line indicates the gain characteristics of the transmission from first speaker 30 to microphone 32, and the solid line indicates that from second speaker 31 to microphone 32.

When the present subject noise frequency stays steadily at 41 Hz, Simulated characteristics comparing section 34 receives this calculation result from frequency calculator 33, and then calculates gains G5, G6 by using the first correction values C1, C2 of transmission elements 12, 13 at 41 Hz, which is the subject frequency to be controlled, as well as by using the second correction values C3, C4 of transmission elements 18, 19 at 41 Hz. In this case, the calculation finds G5=−29 [dB], and G6=−18 [dB]. The respective values agree with the values shown in FIG. 7 as previously discussed. In this case, the difference between G5 and G6 is 11 [dB] which is greater than the threshold value 6 [dB] necessary for the switchover of the speaker, so that the active noise reducing device selects second speaker 31 for the active noise reduction.

Next, a case where the noise frequency increases to 53 Hz is discussed. In this case, the same calculation finds G5=−15 [dB], and G6=−16 [dB]. Since G5 is greater than G6, it is preferable to switch second speaker 31 presently selected over to first speaker 30 from the viewpoint of noise reduction effect, however; the difference is only 1 [dB] between G5 and G6, so that the switchover can produce slight effect. Reviewing FIG. 7 reveals that there is only small difference between G5 and G6 in the frequency range from 45 Hz to 71 Hz. Therefore it is desirable to prevent the control from falling into unstable condition due to frequent switchovers of the speaker within this frequency range rather than to consider the slight effect of noise reduction. The reason why the threshold value of the difference between the respective gain characteristics for switching over the speaker is set at 6 [dB] derives from this theory. At the present noise frequency, i.e. 53 Hz, the difference between G5 and G6 is smaller than the threshold value, i.e. 6 [dB], so that the active noise reducing device does not switch the speaker over to another one.

When the noise frequency further increases to 60 Hz, yet second speaker 31 remains being selected due to the same reason. In the case of FIG. 7, when the noise frequency reaches to 76 Hz, G5 becomes 2 [dB] and G6 becomes −4 [dB], so that the difference between G5 and G6 is 6 [dB] which is not less than the threshold value of 6 [dB]. The active noise reducing device thus switches second speaker 31 over to first speaker 30.

Embodiment 3

The third embodiment uses FIG. 5 as a block diagram of an active noise reducing device in accordance with the third embodiment as the second embodiment uses it. In the second embodiment previously discussed, the active noise reducing device selects the speaker by itself for the noise reduction. This third embodiment addresses a special case of the second embodiment, i.e. dips or peaks are generated in every gain characteristics of the transmission from all the selectable speakers to the microphone at the same frequency band.

Figure 8:
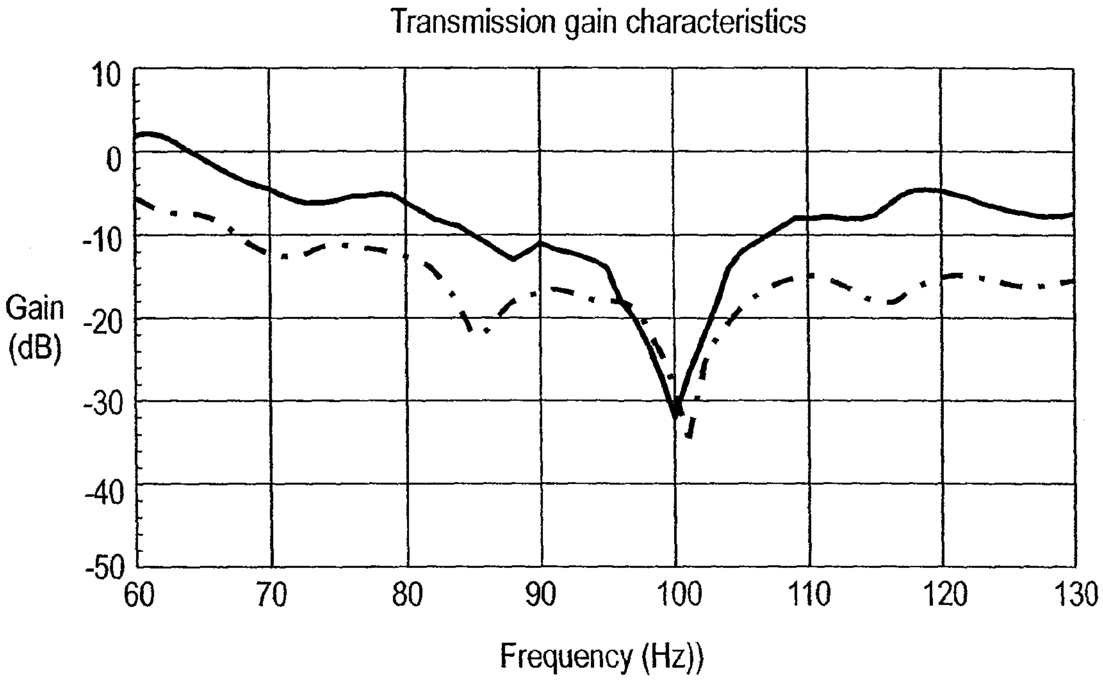
FIG. 8 shows a gain characteristic of the transmission from a first speaker to a microphone of the active noise reducing device shown in FIG. 5 together with a gain characteristics of the transmission from a second speaker to a microphone of the same device in accordance with the third embodiment.

FIG. 8 shows a gain characteristic of the transmission from a first speaker to a microphone of the active noise reducing device shown in FIG. 5 together with a gain characteristics of the transmission from a second speaker to a microphone of the same device in accordance with the third embodiment. In FIG. 8, the gain characteristics from the first speaker to the microphone is drawn with an alternate long and short dash line, and that from the second speaker to the microphone is drawn with a solid line. This is the same as FIGS. 6 and 7. Around 100 Hz among others, both of the characteristics produce a deep dip at this frequency band. The band having such a dip encounters quick phase rotation, so that the control tends to become unstable. This anxiety is already discussed in the first embodiment. When the active noise reducing device selects the speaker by itself, the method described in the second embodiment cannot fully deal with the foregoing problem, i.e. the dips or peaks existing in the same frequency band. This third embodiment addresses the method of avoiding the foregoing problem.

In this embodiment, it is assumed that the active noise reducing device shown in FIG. 5 works in the frequency range from 70 Hz to 120 Hz. Frequency calculator 33 calculates that a present subject noise frequency is 90 Hz. The device compares the gain characteristics (−17 dB) of the transmission from first speaker 30 to microphone 32 with the gain characteristics (−12 dB) of the transmission from second speaker 31 to microphone 32, then the device selects second speaker 31 that gets the maximum value for the noise reduction. To simplify the description, a threshold value of the difference between the two gains is set at "0" (zero), and thus no consideration is needed for the threshold value.

Next, the case where the subject noise frequency changes to 95 Hz is demonstrated hereinafter. In a similar way discussed above, the device compares the gain characteristics (−18 dB) of the transmission from first speaker 30 to microphone 32 with the gain characteristics (−15 dB) of the transmission from second speaker 31 to microphone 32, then the simulated transmission comparing section 34 selects second speaker 31 as the first candidate to be used. However, this selected speaker is not used immediately, and a method described later searches the gain characteristics of the transmission from this selected speaker to the microphone for dips or peaks at this frequency band. When comparing section 34 determines that no dips or peaks are generated, the selected speaker is used for the active noise reduction. If comparing section 34 determines that dips or peaks are generated, the speaker selecting operation discussed previously is repeated for all the speakers except this selected one. This operation allows avoiding the use of the speaker that generates dips or peaks in the transmission gain characteristics at the subject frequency to be controlled, so that the active noise reducing operation becomes more stable.

The method of finding dips or peaks by comparing section 34 is described hereinafter. In this instance, frequency calculator 33 can calculate as fine as 1 Hz as the minimum frequency resolution of noise, and it is assumed that the first correction values, i.e. transmission elements 12, 13, 14 and 15, and the second correction values, i.e. transmission elements 18, 19, 20 and 21 have values at every 1 Hz. In this status, comparing section 34 firstly finds the transmission gain characteristics of second speaker 31 at 94 Hz, namely, by 1 Hz lower than the present subject frequency 95 Hz. FIG. 8 tells that this gain is −14 [dB]. Then comparing section 34 finds the gain characteristics of second speaker 31 at 96 Hz, namely by 1 Hz higher than the present subject frequency 95 Hz. FIG. 8 tells that this gain is −19 [dB].

Next, find respective absolute values of differences between the gain characteristics at two frequencies and that at the present frequency. When at least one of these two absolute values is not less than the threshold value for comparing section 34 to determine the presence of dips or peaks, it is determined that the selected speaker generates dips or peaks at this frequency band, so that the use of the selected speaker is halted. In this instance, assume that the threshold value for comparing section 34 to determine there are dips or peaks is 5 [dB]. Following the foregoing method, find an absolute value of the difference between the gain characteristics at 95 Hz and 94 Hz, and the result is 1 [dB], which is less than the threshold value. Then find an absolute value of the difference between the gain characteristics at 95 Hz and 96 Hz, and the result is 5 [dB], which is not less than the threshold value. Thus it is determined that the gain characteristics of the transmission from second speaker 31 selected at the first place to microphone 32 have a dip or peak at this frequency band.

Based on the preceding result, comparing section 34 repeats the operation similar to what is demonstrated above for all the speakers except second speaker 31. In this instance, since first speaker 1 only remains, there is no need to find which speaker produces the maximum gain; however, when two or more than two speakers remain, the operation should be repeated.

Now the operation similar to what is demonstrated above is repeated by using the gain characteristics of the transmission from first speaker 30 to microphone 32, the results can be read from FIG. 8, i.e. gain at 95 Hz =−18.2 [dB], gain at 94 Hz =−18.0 [dB], gain at 96 Hz =−18.5 [dB]. Then find an absolute value of the difference between the gain at 95 Hz and 94 Hz, and the result is 0.2 [dB], which is less than the threshold value. In a similar way, an absolute value of the difference between 95 Hz and 96 Hz is 0.3 [dB], which is less than the threshold value. Comparing section 34 thus determines that the gain characteristics of the transmission from first speaker 30 to microphone 32 has no dip or peak at this frequency band, thereby switching over the speaker for the active noise reduction. The procedure of this switchover of the speaker is similar to the ones demonstrated in the first and the second embodiments, so that the description thereof is omitted here.

Next, the case where the noise frequency increases up to 100 Hz is demonstrated hereinafter. At 100 Hz, first speaker 30 can obtain the max. gain characteristics of the transmission from the speaker to the microphone, and the gain is −30 [dB]. The gain characteristics of the transmission from first speaker 30 to microphone 32 can be read as −25 [dB] at 99 Hz, and −35 [dB] at 101 Hz. Thus an absolute value of the difference in the gain characteristics between 100 Hz and 99 Hz is 5 [dB], which is not less than the threshold value, and that between 100 Hz and 101 Hz is also 5 [dB], which is not less than the threshold value. Thus it is determined that the gain characteristic of the transmission from selected first speaker 30 to microphone 32 has a dip or peak at this frequency band.

Based on this result, comparing section 34 repeats the foregoing operation excluding first speaker 30 by using the gain characteristics of transmission from the second speaker 31 to microphone 32. The results can be read from FIG. 8 as −33 [dB] at 100 Hz, −28 [dB] at 99 Hz, and −28 [dB] at 101 Hz. Thus an absolute value of the difference in the gain characteristics between 100 Hz and 99 Hz is 5 [dB], which is not less than the threshold value, and that between 100 Hz and 101 Hz is also 5 [dB], which is not less than the threshold value. Thus it is determined again that the gain characteristic of the transmission from second speaker 31 to microphone 32 has a dip or peak at this frequency band. This result tells that all the selectable speakers produce a dip or peak at this frequency band, so that the active noise reducing device stops the operation of the active noise reduction at this frequency band in order to ensure the control stability.

In the first through the third embodiments of the present invention, output switcher 9 of which process is handled by software is employed, however; it can be a mechanical switch or a switch formed of semiconductor such as transistors. In such a case, an adoption of the structure, where the speaker is appropriately switched over based on the information from switchover frequency memory 11 or simulated transmission gain characteristics comparing section 34, will produce an advantage similar to what is discussed previously.

The first through the third embodiments of the present invention show the method through which the switchover of the speaker is determined in response to the noise frequency calculated by frequency calculator 33; however the switchover can be determined directly based on engine pulses of engine 1. Because a frequency component of the subject noise is a harmonic frequency synchronized with the engine rotation.

In the first through the third embodiments of the present invention, two speakers are used as the secondary noise generators, however; the number of speakers can be three or more than three. In such a case, plural power amplifiers and simulated signal generators corresponding to the respective speakers are prepared, and one of the speakers is selected for an actual use, thereby obtaining an advantage similar to what is discussed in the embodiments.

INDUSTRIAL APPLICABILITY

An active noise reducing device of the present invention switches a speaker over to another one both working as secondary noise generators for radiating an output from an adaptive notch filter as secondary noise, so that the device operates in a stable manner even when dips or peaks are produced in the gain characteristics of the transmission from the speaker to a microphone. The foregoing structure also suppresses the occurrence of a distorted sound due to an excessive input or an abnormal sound due to divergence, so that ideal noise reduction effect can be expected. The device is thus useful for cars.

What is claimed is:

1. An active noise reducing device comprising:

a cosine wave generator for generating a cosine wave signal synchronized with a frequency of noise;

a sine wave generator for generating a sine wave signal synchronized with the frequency of the noise;

a first one-tap adaptive filter for receiving a reference cosine wave which is an output signal from the cosine wave generator;

a second one-tap adaptive filter for receiving a reference sine wave which is an output signal from the sine wave generator;

an adder for adding an output signal from the first one-tap adaptive filter to an output signal from the second one-tap adaptive filter;

a plurality of secondary noise generators for generating a secondary noise by using an output signal from the adder;

a switcher, disposed between the adder and the plurality of secondary noise generators, for selecting one of the plurality of secondary noise generators by selectively inputting the adder output signal to one of the plurality of secondary noise generators;

a residual signal detector for detecting a residual signal produced by interference between the noise and the secondary noise which is generated by the secondary noise generator selected by the switcher, and wherein the switcher performs the selection based on switchover frequencies relating to transmission gain peaks and transmission gain dips between the plurality of secondary noise generators and the residual signal detector;

a simulated signal generator, including a plurality of correction values simulating transmission characteristics from the plurality of the secondary noise generators to the residual signal detector, for outputting a simulated cosine wave signal and a simulated sine wave signal both being corrected with the correction value between the secondary noise generator, which receives the reference cosine wave signal and the reference sine wave signal and is selected by the switcher, and the residual signal detector; and a coefficient updating section for updating respective filter coefficients of the first one-tap adaptive filter and the second one-tap adaptive filter so that noise at the residual signal detector can be minimized by the respective output signals from the residual signal detector and the simulated signal generator.

2. The active noise reducing device of claim 1, wherein the switcher outputs a switching signal in response to a frequency of noise.

3. The active noise reducing device of claim 1, wherein the switcher stops updating the respective filter coefficients of the first one-tap adaptive filter and the second one-tap adaptive filter at the coefficient updating section when one of the secondary noise generators is switched over, and multiplies the output signal from the adder by a coefficient which decreases from 1 to 0 step by step, and starts updating the coefficients of the adaptive filters at the coefficient updating section for outputting a switching signal after the coefficient reaches 0.

4. The active noise reducing device of claim 1, wherein every time a frequency of the noise changes, the switcher compares gain values with each other, at a present frequency, among a plurality of correction values simulating respective transmission characteristics from the plurality of secondary noise generators to the residual signal generator, and selects the secondary noise generator that makes the value maximum.

5. The active noise reducing device of claim 4, wherein the switcher outputs a switching signal only when an absolute value of a difference is not less than a given value, and wherein the difference is a difference between a gain value, at a present frequency among correction values simulating a transmission characteristics from the secondary noise generator that makes the value maximum to the residual signal detector and a gain value, at the present frequency among correction values simulating a transmission characteristics from a secondary noise generator selected before the present and now in use to the residual signal detector.

6. The active noise reducing device of claim 4, wherein the switcher re-selects one of the secondary noise generators excluding the selected secondary noise generator when at least one of absolute values is not less than a given value, and wherein the absolute value is an absolute value of a difference between a gain value at a present frequency of correction values simulating a transmission characteristics from the secondary noise generator that makes the value maximum to the residual signal detector and a gain value having the correction value and being at a frequency lower than and yet closest to the present frequency, and another absolute value is an absolute value of a difference between the gain value at the present frequency of correction values simulating the transmission characteristics from the secondary noise generator that makes the value maximum to the residual signal detector and a gain value having the correction value and being at a frequency higher than and yet closest to the present frequency.

7. The active noise reducing device of claim 6, wherein when the switcher cannot select one of the secondary noise generators, the device does not select any one of the secondary noise generators, and does not do anything for noise reduction.

8. The active noise reducing device of claim 2, wherein the switcher stops updating the respective filter coefficients of the first one-tap adaptive filter and the second one-tap adaptive filter at the coefficient updating section when one of the secondary noise generators is switched over, and multiplies the output signal from the adder by a coefficient which decreases from 1 to 0 step by step, and starts updating the coefficients of the adaptive filters at the coefficient updating section for outputting a switching signal after the coefficient reaches 0.

9. The active noise reducing device of claim 2, wherein every time a frequency of the noise changes, the switcher compares gain values with each other, at a present frequency, among a plurality of correction values simulating respective transmission characteristics from the plurality of secondary noise generators to the residual signal generator, and selects the secondary noise generator that makes the value maximum.

10. The active noise reducing device of claim 9, wherein the switcher outputs a switching signal only when an absolute value of a difference is not less than a given value, and wherein the difference is a difference between a gain value, at a present frequency among correction values simulating a transmission characteristics from the secondary noise generator that makes the value maximum to the residual signal detector and a gain value, at the present frequency among correction values simulating a transmission characteristics from a secondary noise generator selected before the present and now in use to the residual signal detector.

11. The active noise reducing device of claim 9, wherein the switcher re-selects one of the secondary noise generators excluding the selected secondary noise generator when at least one of absolute values is not less than a given value, and wherein the absolute value is an absolute value of a difference between a gain value at a present frequency of correction values simulating a transmission characteristics from the secondary noise generator that makes the value maximum to the residual signal detector and a gain value having the correction value and being at a frequency lower than and yet closest to the present frequency, and another absolute value is an absolute value of a difference between the gain value at the present frequency of correction values simulating the transmission characteristics from the secondary noise generator that makes the value maximum to the residual signal detector and a gain value having the correction value and being at a frequency higher than and yet closest to the present frequency.

12. The active noise reducing device of claim 11, wherein when the switcher cannot select one of the secondary noise generators, the device does not select any one of the secondary noise generators, and does not do anything for noise reduction.

* * * * *